US012642706B2

(12) United States Patent (10) Patent No.: US 12,642,706 B2

Wheldrake (45) Date of Patent: Jun. 2, 2026

(54) METHOD OF MANUFACTURING A COMPONENT FOR A WOUND DRESSING

(71) Applicant: T.J.Smith and Nephew, Limited, Hull (GB)

(72) Inventor: Amy Nicole Wheldrake, Goole (GB)

(73) Assignee: T.J.Smith and Nephew, Limited, Hull (GB)

( * ) Notice: Subject to any disclaimer, the term of this patent is extended or adjusted under 35 U.S.C. 154(b) by 696 days.

(21) Appl. No.: 17/422,143

(22) PCT Filed: Jan. 10, 2020

(86) PCT No.: PCT/EP2020/050574

§ 371 (c)(1),
(2) Date: Jul. 9, 2021

(87) PCT Pub. No.: WO2020/144347

PCT Pub. Date: Jul. 16, 2020

(65) Prior Publication Data

US 2022/0087869 A1 Mar. 24, 2022

(30) Foreign Application Priority Data

Jan. 11, 2019 (GB) ...................................... 1900407

(51) Int. Cl.
*A61F 13/05* (2024.01)
*A61F 13/00* (2024.01)
*A61F 13/01* (2024.01)
(52) U.S. Cl.
CPC ........ *A61F 13/05* (2024.01); *A61F 13/00987* (2013.01); *A61F 13/01029* (2024.01);
(Continued)

(58) Field of Classification Search
CPC ................ A61F 13/05; A61F 13/00987; A61F 13/01029; A61F 13/01042;
(Continued)

(56) References Cited

U.S. PATENT DOCUMENTS 3,561,441 A * 2/1971 Lombardi ......... A61F 13/01021
602/44
3,972,328 A 8/1976 Chen
(Continued)

FOREIGN PATENT DOCUMENTS

AU 2015200669 A1 3/2015
CN 104109922 A 10/2014
(Continued)

OTHER PUBLICATIONS

International Search Report and Written Opinion for Application No. PCT/EP2020/050574, mailed on Mar. 12, 2020, 10 pages.
(Continued)

*Primary Examiner* — Ophelia A Hawthorne

(74) *Attorney, Agent, or Firm* — Knobbe, Martens, Olson & Bear, LLP

(57) ABSTRACT

There is provided a method of manufacturing a component for a wound dressing comprising the step of mechanically manipulating a yarn with a machine to form a discrete structure having a predetermined shape wherein the discrete structure is in a form suitable for incorporation into or for use as a wound dressing without changes to the dimensions of said discrete structure; components formed by the method of manufacturing the component, the use of the component in or as a wound dressing, and the use of the component or wound dressing in a method of treating a wound. The disclosed technology further relates to a machine configured to produce the component for a wound dressing according to the method; a computer program product comprising
(Continued)

instructions to cause the machine to execute the steps of the method and a non-transitory computer readable medium having stored thereon the computer program product.

20 Claims, 7 Drawing Sheets

(52) U.S. Cl.
CPC ............... *A61F 2013/00238* (2013.01); *A61F 13/01042* (2024.01)

(58) Field of Classification Search
CPC ........ A61F 2013/00238; A61F 13/0209; A61F 2013/15073; A61F 2013/00536; A61M 1/915; A61M 1/985
See application file for complete search history.

(56) References Cited

U.S. PATENT DOCUMENTS

| | | | |
|---|---|---|---|
| 4,029,598 A | 6/1977 | Neisius et al. |
| 4,728,499 A | 3/1988 | Fehder |
| 4,813,942 A | 3/1989 | Alvarez |
| 4,897,297 A | 1/1990 | Zafiroglu |
| 5,056,510 A | 10/1991 | Gilman |
| 5,181,905 A | 1/1993 | Flam |
| 5,238,732 A | 8/1993 | Krishnan |
| 5,258,220 A | 11/1993 | Joseph |
| 5,549,584 A | 8/1996 | Gross |
| 5,707,499 A | 1/1998 | Joshi et al. |
| 5,759,570 A | 6/1998 | Arnold |
| 5,852,126 A | 12/1998 | Barnard et al. |
| 6,071,267 A | 6/2000 | Zamierowski |
| 6,626,891 B2 | 9/2003 | Ohmstede |
| 6,667,424 B1 | 12/2003 | Hamilton et al. |
| 6,685,681 B2 | 2/2004 | Lockwood et al. |
| 6,752,794 B2 | 6/2004 | Lockwood et al. |
| 6,936,037 B2 | 8/2005 | Bubb et al. |
| 6,951,553 B2 | 10/2005 | Bubb et al. |
| 6,962,064 B1 | 11/2005 | Hardee et al. |
| 6,979,324 B2 | 12/2005 | Bybordi et al. |
| 7,070,584 B2 | 7/2006 | Johnson et al. |
| 7,108,683 B2 | 9/2006 | Zamierowski |
| 7,216,651 B2 | 5/2007 | Argenta et al. |
| 7,361,184 B2 | 4/2008 | Joshi |
| 7,381,859 B2 | 6/2008 | Hunt et al. |
| 7,605,298 B2 | 10/2009 | Bechert et al. |
| 7,622,629 B2 | 11/2009 | Aali |
| 7,625,362 B2 | 12/2009 | Boehringer et al. |
| 7,700,819 B2 | 4/2010 | Ambrosio et al. |
| 7,718,249 B2 | 5/2010 | Russell et al. |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,811,269 B2 | 10/2010 | Boynton et al. |
| 7,910,791 B2 | 3/2011 | Coffey |
| 7,922,703 B2 | 4/2011 | Riesinger |
| 7,959,624 B2 | 6/2011 | Riesinger |
| 7,976,519 B2 | 7/2011 | Bubb et al. |
| 8,062,331 B2 | 11/2011 | Zamierowski |
| 8,152,785 B2 | 4/2012 | Vitaris |
| 8,162,907 B2 | 4/2012 | Heagle |
| 8,235,972 B2 | 8/2012 | Adahan |
| 8,241,261 B2 | 8/2012 | Randolph et al. |
| 8,303,552 B2 | 11/2012 | Weston |
| 8,372,049 B2 | 2/2013 | Jaeb et al. |
| 8,372,050 B2 | 2/2013 | Jaeb et al. |
| 8,425,478 B2 | 4/2013 | Olson |
| 8,513,481 B2 | 8/2013 | Gergely et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,628,505 B2 | 1/2014 | Weston |
| 8,641,691 B2 | 2/2014 | Fink et al. |
| 8,663,198 B2 | 3/2014 | Buan et al. |
| 8,795,243 B2 | 8/2014 | Weston |
| 8,795,800 B2 | 8/2014 | Evans |
| 8,956,336 B2 | 2/2015 | Haggstrom et al. |
| 9,012,714 B2 | 4/2015 | Fleischmann |
| 9,061,095 B2 | 6/2015 | Adie et al. |
| 9,067,003 B2 | 6/2015 | Buan et al. |
| 9,127,665 B2 | 9/2015 | Locke et al. |
| 9,220,822 B2 | 12/2015 | Hartwell |
| 9,302,033 B2 | 4/2016 | Riesinger |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,427,505 B2 | 8/2016 | Askem et al. |
| 9,440,001 B2 | 9/2016 | Kettlewell et al. |
| 9,452,248 B2 | 9/2016 | Blott et al. |
| 9,629,986 B2 | 4/2017 | Patel et al. |
| 9,681,993 B2 | 6/2017 | Wu et al. |
| 9,682,179 B2 | 6/2017 | May |
| 9,795,725 B2 | 10/2017 | Joshi et al. |
| 9,820,888 B2 | 11/2017 | Greener et al. |
| 9,829,471 B2 | 11/2017 | Hammond et al. |
| 9,844,473 B2 | 12/2017 | Blott et al. |
| 9,962,474 B2 | 5/2018 | Greener |
| 10,016,309 B2 | 7/2018 | Hartwell |
| 10,046,096 B2 | 8/2018 | Askem et al. |
| 10,058,642 B2 | 8/2018 | Weston |
| 10,076,449 B2 | 9/2018 | Allen et al. |
| 10,188,555 B2 | 1/2019 | Vitaris et al. |
| 10,201,644 B2 | 2/2019 | Haggstrom et al. |
| 10,328,188 B2 | 6/2019 | Deutsch et al. |
| 10,493,184 B2 | 12/2019 | Collinson et al. |
| 2003/0125646 A1 | 7/2003 | Whitlock |
| 2004/0057855 A1 | 3/2004 | Gerlach et al. |
| 2004/0126413 A1 | 7/2004 | Sigurjonsson et al. |
| 2004/0265534 A1 | 12/2004 | Curro et al. |
| 2006/0009744 A1 | 1/2006 | Erdman et al. |
| 2007/0040454 A1 | 2/2007 | Freudenberger et al. |
| 2007/0225663 A1 | 9/2007 | Watt et al. |
| 2007/0255194 A1 | 11/2007 | Gudnason et al. |
| 2008/0031748 A1 | 2/2008 | Ihle et al. |
| 2008/0132821 A1 | 6/2008 | Propp et al. |
| 2009/0125004 A1 | 5/2009 | Shen et al. |
| 2009/0157024 A1 | 6/2009 | Song |
| 2009/0216168 A1 | 8/2009 | Eckstein |
| 2009/0234306 A1 | 9/2009 | Vitaris |
| 2009/0299306 A1 | 12/2009 | Buan |
| 2010/0030178 A1 | 2/2010 | Macmeccan et al. |
| 2010/0036334 A1 | 2/2010 | Heagle et al. |
| 2010/0125258 A1 | 5/2010 | Coulthard et al. |
| 2010/0259406 A1 | 10/2010 | Caso et al. |
| 2010/0318052 A1 | 12/2010 | Ha et al. |
| 2011/0004172 A1 | 1/2011 | Eckstein et al. |
| 2011/0209505 A1 | 9/2011 | Thompson et al. |
| 2011/0224631 A1 | 9/2011 | Simmons et al. |
| 2012/0051945 A1 | 3/2012 | Orndorff et al. |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0144227 A1 | 6/2013 | Locke et al. |
| 2013/0165878 A1 | 6/2013 | Heagle |
| 2013/0296762 A1 | 11/2013 | Toth |
| 2013/0302545 A1 | 11/2013 | Schnelker et al. |
| 2014/0005616 A1 | 1/2014 | Moreland et al. |
| 2014/0114268 A1 | 4/2014 | Auguste et al. |
| 2014/0135721 A1 | 5/2014 | Riesinger |
| 2014/0200533 A1 | 7/2014 | Whyte et al. |
| 2014/0249495 A1* | 9/2014 | Mumby .............. A61F 13/0226 604/385.01 |
| 2014/0276490 A1 | 9/2014 | Locke et al. |
| 2014/0322512 A1 | 10/2014 | Pham et al. |
| 2015/0032035 A1 | 1/2015 | Banwell et al. |
| 2015/0104486 A1 | 4/2015 | Bonnefin et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2016/0000611 A1 | 1/2016 | Niederauer et al. |

(56) References Cited

U.S. PATENT DOCUMENTS

| | | | |
|---|---|---|---|
| 2016/0051413 A1 | 2/2016 | Moreland et al. | |
| 2016/0074251 A1 | 3/2016 | Strube et al. | |
| 2016/0095754 A1 | 4/2016 | Andrews et al. | |
| 2016/0193086 A1 | 7/2016 | Castle | |
| 2016/0298620 A1 | 10/2016 | Cordoba et al. | |
| 2017/0065458 A1 | 3/2017 | Mumby et al. | |
| 2017/0119595 A1 | 5/2017 | Carla et al. | |
| 2017/0128642 A1 | 5/2017 | Buan | |
| 2017/0281825 A1 | 10/2017 | Pins et al. | |
| 2017/0368239 A1 | 12/2017 | Askem et al. | |
| 2018/0133378 A1 | 5/2018 | Askem et al. | |
| 2018/0318476 A1 | 11/2018 | Askem et al. | |
| 2019/0015258 A1* | 1/2019 | Gowans | A61F 13/05 |
| 2019/0021912 A1 | 1/2019 | Cotton et al. | |
| 2019/0125590 A1 | 5/2019 | Rehbein et al. | |
| 2019/0133841 A1 | 5/2019 | Bewick-Sonntag et al. | |
| 2019/0375202 A1* | 12/2019 | Singletary | F41H 5/0478 |
| 2020/0008981 A1 | 1/2020 | Wheldrake | |
| 2020/0121833 A9 | 4/2020 | Askem et al. | |
| 2022/0002916 A1 | 1/2022 | Wheldrake | |
| 2022/0296426 A1 | 9/2022 | Wheldrake | |
| 2022/0331481 A1 | 10/2022 | Wheldrake | |

FOREIGN PATENT DOCUMENTS

| | | | |
|---|---|---|---|
| CN | 108103628 A | 6/2018 | |
| DE | 3443101 A1 | 5/1986 | |
| DE | 20022041 U1 | 3/2001 | |
| EP | 0340018 A2 | 11/1989 | |
| EP | 1350872 A1 | 10/2003 | |
| EP | 1476217 B1 | 3/2008 | |
| EP | 1904011 A1 | 4/2008 | |
| EP | 1955887 A2 | 8/2008 | |
| EP | 2462908 A1 | 6/2012 | |
| EP | 2578193 A1 | 4/2013 | |
| EP | 2777662 A1 | 9/2014 | |
| EP | 3628289 B1 | 11/2021 | |
| EP | 3908240 A1 | 11/2021 | |
| FR | 1163907 A | 10/1958 | |
| GB | 1255395 A | 12/1971 | |
| GB | 2307180 B | 6/2000 | |
| GB | 2468905 A | 9/2010 | |
| GB | 2496310 A | 5/2013 | |
| GB | 2504873 A | 2/2014 | |
| GB | 2512841 A | 10/2014 | |
| WO | WO-8300742 A1 | 3/1983 | |
| WO | WO-9216245 A1 | 10/1992 | |
| WO | WO-9325379 A1 | 12/1993 | |
| WO | WO-9605873 A1 | 2/1996 | |
| WO | WO-03008680 A1 | 1/2003 | |
| WO | WO-2004077387 A1 | 9/2004 | |
| WO | WO-2005046760 A1 | 5/2005 | |
| WO | WO-2005105180 A1 | 11/2005 | |
| WO | WO-2007025544 A1 | 3/2007 | |
| WO | WO-2007113597 A2 | 10/2007 | |
| WO | WO-2008039223 A1 | 4/2008 | |
| WO | WO-2009019227 A2 | 2/2009 | |
| WO | WO-2009124100 A1 | 10/2009 | |
| WO | WO-2009147402 A2 | 12/2009 | |
| WO | WO-2009158128 A2 | 12/2009 | |
| WO | WO-2010142959 A2 | 12/2010 | |
| WO | WO-2011135285 A1 | 11/2011 | |
| WO | WO-2011135286 A1 | 11/2011 | |
| WO | WO-2011135287 A1 | 11/2011 | |
| WO | WO-2011144888 A1 | 11/2011 | |
| WO | WO-2012131237 A1 | 10/2012 | |
| WO | WO-2012143665 A1 | 10/2012 | |
| WO | WO-2013010907 A1 | 1/2013 | |
| WO | WO-2013064852 A1 | 5/2013 | |
| WO | WO-2013079947 A1 | 6/2013 | |
| WO | WO-2013083800 A1 | 6/2013 | |
| WO | WO-2013090810 A1 | 6/2013 | |
| WO | WO-2013149078 A1 | 10/2013 | |
| WO | WO-2014008348 A2 | 1/2014 | |
| WO | WO-2014016759 A1 | 1/2014 | |
| WO | WO-2014020440 A1 | 2/2014 | |
| WO | WO-2014108476 A1 | 7/2014 | |
| WO | WO-2015022334 A1 | 2/2015 | |
| WO | WO-2015022340 A1 | 2/2015 | |
| WO | WO-2016018448 A1 | 2/2016 | |
| WO | WO-2016174048 A1 | 11/2016 | |
| WO | WO-2017173069 A1 | 10/2017 | |
| WO | WO-2017192979 A1 | 11/2017 | |
| WO | WO-2017196888 A1 | 11/2017 | |
| WO | WO-2018037075 A1 | 3/2018 | |
| WO | WO-2018164803 A1 | 9/2018 | |

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

International Preliminary Report on Patentability and Written Opinion for Application No. PCT/EP2020/050574, mailed on Jul. 22, 2021, 8 pages.

Kendall ULTEC Hydrocolloid Dressing (4"x4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Technology Watch, May 1989, 1 page.

Zhang X., et al., "Application of Knitting Structure Textiles in Medical Areas," AUTEX Research Journal, Nov. 2017, 11 pages.

Definition of "layer", The Free Dictionary by Farlex, webpage accessed Sep. 12, 2024, 7 pages. URL: https://www.thefreedictionary.com/layer.

* cited by examiner

200

METHOD OF MANUFACTURING A COMPONENT FOR A WOUND DRESSING

CROSS-REFERENCE TO RELATED APPLICATIONS

This application is a U.S. national stage application of International Patent Application No. PCT/EP2020/050574, filed Jan. 10, 2020, which claims priority to U.K. Provisional Application No. 1900407.6, filed on Jan. 11, 2019; the disclosure of each of which is hereby incorporated by reference in its entirety.

FIELD

The disclosed technology relates to a method of manufacturing a component for a wound dressing. The disclosed technology also relates to components formed by the method of manufacturing the component, the use of the component in or as a wound dressing, and the use of the component or wound dressing in a method of treating a wound.

The disclosed technology further relates to a machine configured to produce the component for a wound dressing according to the method; a computer program product comprising instructions to cause the machine to execute the steps of the method and a non-transitory computer readable medium having stored thereon the computer program product.

BACKGROUND

Many different types of wound dressings are known for aiding the healing process of a human or animal. These different types of wound dressing include many different types of materials and layers, for example, gauze, pads, foam pads or multi-layer wound dressings. Components used in wound dressings are typically produced as roll good and subsequently cut to the required size. Although this approach may be acceptable, it can result in significant amounts of wastage and, for certain types of material, may require multiple additional processing steps to ensure that the component is suitable for use in a wound dressing, for example sealing and or smoothing cut edges.

Topical negative pressure therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like. Wound dressings used in such therapy can require specific components or layers to facilitate the application of reduced pressure.

One such component is a spacer layer which enables gaseous flow, allowing negative pressure to be applied and supporting the transport of wound exudate. Spacer layers typically have a higher cost than other traditional wound dressing materials.

In addition to the high cost, the material can pose further manufacturing issues. Whereas traditional materials, such as nonwovens when processed as a roll good can be rotary cut, spacer fabrics are typically woven or knitted and are therefore less stable requiring a more labour intense process such as flatbed cutting to produce a suitable final product.

SUMMARY

Embodiments of the present disclosure are directed to a method of manufacturing a component for a wound dressing. The disclosed technology also relates to components formed by the method of manufacturing the component, the use of the component in or as a wound dressing, and the use of the component or wound dressing in a method of treating a wound.

According to a first aspect of the invention is provided a method of manufacturing a component for a wound dressing comprising the step of mechanically manipulating a yarn with a machine to form a discrete structure having a predetermined shape wherein the discrete structure is in a form suitable for incorporation into or for use as a wound dressing without changes to the dimensions of said discrete structure.

Without changes to the dimensions of the discrete structure means that the shape of the discrete structure remains substantially unchanged after formation by the method of the first aspect of the invention. Subsequent processing which does not alter the shape of the discrete structure may occur, for example the application of a coating such as an antimicrobial substance. Similarly, the discrete structure may be trimmed to remove loose ends or similar. By substantially unchanged is meant that the size of the structure does not change by more than 10%, more than 5%, 2% or 1%.

Mechanically manipulating a yarn with a machine means that the manipulation is carried out by a mechanical process, i.e. not by hand.

By predetermined shape means that the machine is programmed, set up or manufactured to make the discrete structure in a specific shape.

Preferably the discrete structure is formed by knitting or weaving the yarn, preferably by knitting the yarn.

The predetermined shape is preferably determined by the shape of the wound or body part to which the dressing is to be applied.

According to a second aspect of the invention is provided a discrete structure formed according to the method of the first aspect.

The discrete structure may be a spacer fabric.

The discrete structure may comprise an absorbent yarn.

Preferably the absorbent yarn is distributed through the discrete structure in a predetermined pattern. Preferably the absorbent yarn is laid into the discrete structure.

The discrete structure may comprise a void suitable for incorporating an additional component of a wound dressing within said void.

According to a third aspect of the invention is provided a machine configured to produce a component for a wound dressing according to the method of the first aspect.

According to a fourth aspect of the invention is provided a computer program product comprising instructions to cause the device of the third aspect to execute the steps of the method of the first aspect.

According to a fifth aspect of the invention is provided a non-transitory computer readable medium having stored thereon the computer program product of the fourth aspect.

According to an sixth aspect of the invention there is provided a system comprising at least one computing device, the computing device comprising:

at least one processor; and at least one memory storing instructions which, when executed by the at least one processor, cause the computer device to perform the method of the first aspect.

According to a seventh aspect of the invention is provided the use of the discrete structure of the second aspect or produced by the method of the first aspect in or as a wound dressing, or the use of said discrete structure or wound dressing in a method of treating a wound

BRIEF DESCRIPTION OF DRAWINGS

Embodiments of the present disclosure will now be described hereinafter, by way of example only, with reference to the accompanying drawings in which.

DESCRIPTION OF EMBODIMENTS

Figure 1:
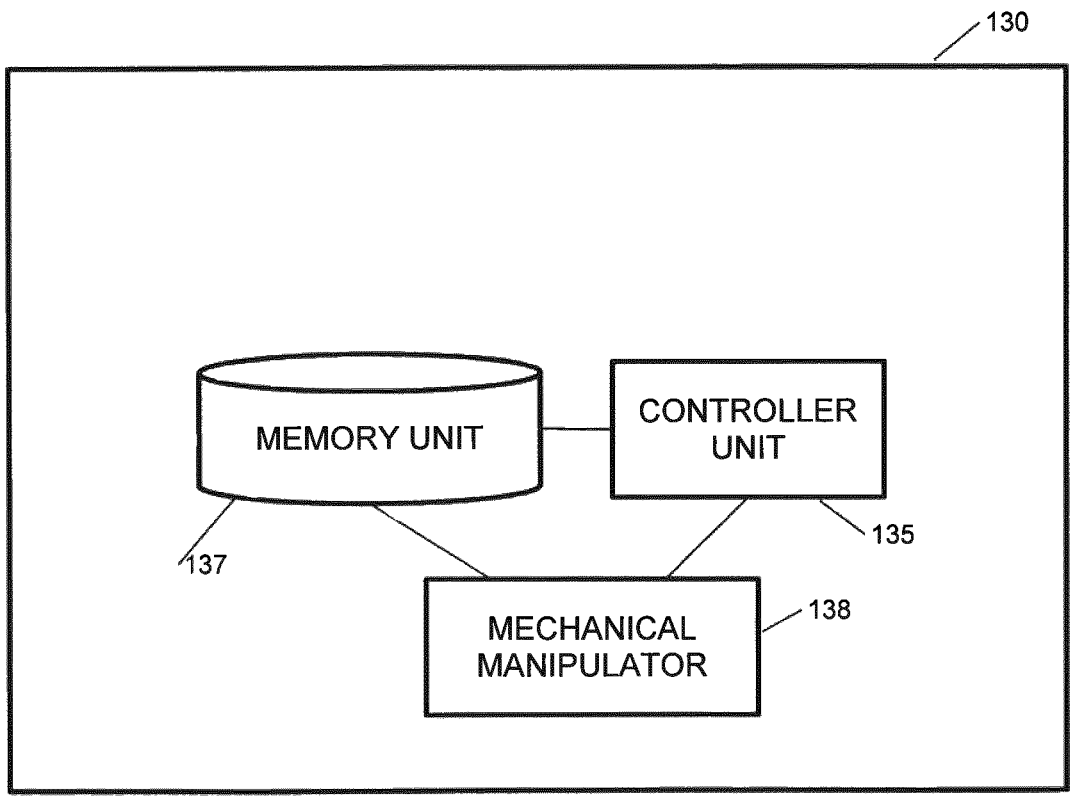
FIG. 1 is a schematic block diagram of an embodiment of a machine according to the third aspect of the invention.

The present invention relates to a method of manufacturing a component for a wound dressing comprising the step of mechanically manipulating a yarn with a machine to form a discrete structure having a predetermined shape wherein the discrete structure is in a form suitable for incorporation into or for use as a wound dressing without changes to the dimensions of said discrete structure.

By forming a discrete structure that is suitable for incorporation into or for use as a wound dressing without changes to the dimensions of said discrete structure, a wound dressing can be additively manufactured. A wound dressing can therefore be formed that provides a significant reduction in the amount of waste produced and is therefore both more environmentally friendly and cheaper to produce. In addition, the finish of the product can be more precise allowing for the prevention of loose fibres and rough edges. This leads to greater comfort to the patient and/or reduces the requirement for additional shielding layers between the wound and the additional components. Furthermore, it is possible to create bespoke wound dressings for a particular patient, wound site or type of wound which further aids patient comfort.

The discrete structure may be formed using more than one yarn. The discrete structure may be formed from a plurality of yarns. The plurality of yarns may be different types of yarn. Each yarn may be selected to provide the discrete structure with different properties. The yarns may be independently selected from support yarns, such as cotton, viscose, lyocell, polylactic acid (PLA), polyester, polypropylene, polyamide, ultra high molecular weight polyethylene (UHMWPE), high density polyethylene (HDPE), absorbent yarns, such as gelling yarns, superabsorbent yarns such as carboxymethyl cellulose (CMC yarns), textured yarns such as polyester/viscose blends elastomeric yarns such as spandex or combinations thereof. Yarns may be coated with coatings such as polyvinyl chloride (PVC), polyurethane (PU), or silicones. Yarns may be finished with hydrophobic or hydrophilic treatments. The yarns may be produced from a specific type of fibre or a blend thereof or may be produced from a combination of different yarns, fibres or filaments.

The discrete structure may be constructed such that different regions of the discrete structure have different properties. Different regions of the discrete structure may be formed from different yarns or from different proportions of a combination of a plurality of yarns. Different regions of the discrete structure may be formed from different densities of yarn. The discrete structure may be formed of a plurality of layers. Each of the layers may have different properties and may be formed from different yarns. Each of the layers may themselves have different regions formed from different yarns.

The discrete structure may comprise an absorbent yarn. The absorbent yarn may comprise a superabsorbent yarn.

Preferably the absorbent yarn may be distributed through the discrete structure in a predetermined pattern. Certain regions of the discrete structure may be formed from an absorbent yarn or have a higher percentage of an absorbent yarn incorporated within them than in the remaining regions of the discrete structure. The discrete structure may further comprise a support yarn. A support yarn retains its structure and strength on contact with liquids such as wound exudate. Suitable support yarns may be formed from any suitable support materials known in the art, or may be a mixture of two or more support materials. The support materials may comprise textile materials, and may comprise natural materials (e.g. cotton), natural materials which have been modified (e.g. cellulosic fibres such as viscose or lyocell (sold under the trade name TENCEL)), or synthetic (e.g. polyester, polypropylene or polyamide) materials. Different materials and fibres thereof have different characteristics in terms of tensile strength and absorbency, and appropriate support materials may be chosen according to the desired characteristics. In addition, a combination of two or more support materials may be used in order to achieve the desired characteristics. Preferably, the support materials are natural materials or fibres thereof which have been modified or synthetic materials. More preferably, the support materials are cellulosic materials or fibres thereof or polyester or polyamide materials or fibres thereof, most preferably viscose, polyester or polyamide materials or fibres thereof.

The discrete structure is preferably for use in a negative pressure wound dressing. The discrete structure is particularly of use in a negative pressure wound dressing when the discrete structure is a spacer fabric. Spacer fabrics retain the integrity of their open structure when a negative pressure is applied, maintaining the application of the negative pressure to the wound site in the presence of wound exudate.

Preferably therefore at least a portion of the discrete structure retains its integrity on application of negative pressure in the presence of wound exudate. By retaining its integrity is intended to mean that the discrete structure substantially retains its original volume, i.e. the discrete structure has a volume when negative pressure is applied which is at least 50% of its original volume, preferably at least 60%, at least 70%, at least 80% or at least 90%.

The entire discrete structure may retain its integrity when negative pressure is applied or alternatively only specific regions of the discrete structure may retain their integrity when negative pressure is applied and other specific regions may be constructed to deliberately collapse. This may be achieved by the method of the first aspect of the invention by forming the discrete structure in a predetermined pattern in which different regions of the discrete structure have different compression ratios, i.e. under negative pressure certain areas will collapse and others will not.

This enables the properties of the discrete structure and hence the wound dressing in which it is incorporated to be fine tuned for the appropriate end use. For example the application of reduced pressure may be more easily controlled and applied to specific areas of a wound site or at specific times by forming the discrete structure with specific regions which maintain their integrity on application of reduced pressure in the presence of wound exudate.

According to a third aspect of the invention is provided a machine configured to produce a component for a wound dressing according to the method of the first aspect. Preferably the discrete structure is formed by knitting or weaving the yarn using a knitting machine or loom. Preferably the discrete structure is knitted using a knitting machine. By a knitting machine is meant any device capable of mechanically producing a knitted structure. By a loom is meant any device capable of mechanically producing a woven structure.

The yarn may be knitted or woven by any suitable means. For example the yarn may be warp- or weft-knitted or plain, twill, sateen, or basket woven.

The yarn may incorporate other components useful in wound treatment. For example, medicaments, antimicrobial, antibacterial or antiseptic materials, or odour control materials. Suitable components are known to the skilled person as are materials which incorporate such components. Alternatively, such components may be subsequently applied to the yarn for example by dipping or spraying the yarn with a solution comprising the component.

Additional yarns may be laid into the discrete structure. Inlaid (or laid-in) fabric consists of a ground structure of knitted or overlapped (warp knitted) threads that hold in position other non-knitted threads which were incorporated (laid-in) into the structure during the same knitting cycle. An inlaid yarn is never formed into a knitted loop, although in weft knitting, when using only one bed of needles, it is necessary to form the inlay yarn into occasional tuck stitches in order to hold it in the technical back of the structure.

When weft knitting with two sets of needles, or when overlapping on the front guide bar of a warp knitting machine, it is possible to introduce the inlaid yarn into the structure merely by supplying the yarn across the backs of the needles (the front of the machine) in order to trap the yarn in the fabric.

Inlaid yarns are trapped inside double needle bed fabrics by the loops or overlaps; and towards the back of single needle bed fabrics by the sinker loops or underlaps.

Dependent upon the fabric construction and the types of yarns employed, laying-in may be used to modify one or more of the following properties of a knitted structure: stability, elastic stretch and recovery, handle, weight, surface 'interest', and visual appearance.

Preferably the laid in yarn is an absorbent yarn or a superabsorbent yarn. The superabsorbent yarn may comprise any suitable superabsorbent material. A superabsorbent material is typically capable of absorbing many times its own mass of water, for example up to 200, 300 or more times its own mass of water.

Examples of suitable superabsorbent materials include a polysaccharide or modified polysaccharide, a polyvinylpyrrolidone, a polyvinyl alcohol, a polyvinyl ether, a polyurethane, a polyacrylate, a polyacrylamide, collagen, a cellulose, gelatin, or mixtures thereof.

The laid in yarn may be laid in to specific regions of the discrete structure, for example an absorbent yarn may be laid into the central portion of the discrete structure to increase absorbency of that region and encourage exudate from the wound to move towards the centre of the dressing.

Laying-in offers the possibility of introducing fancy, unusual, and/or inferior or superior yarns whose physical properties such as thickness (linear density, count), low strength, irregular surface or cross-sectional area, elasticity or lack of elasticity render them difficult to knit into intermeshed loops.

In certain embodiments an absorbent yarn may be laid into the discrete structure. Alternatively, the laid in yarn may be introduced to increase stability. Alternatively the inlaid yarn may be an elastomeric yarn, in which case the elastic stretch and recovery properties of the fabric may be improved.

Discrete structures according to the second aspect of the invention may take various forms, for example sheets, bandages, tubular structures, or any other shape which is suitable for use as a wound dressing or component in a wound dressing. Such structures are typically square or rectangular in shape, or are shaped for conformity with a particular area of the body. Other structures according to the invention may be formed in three-dimensional shapes. The discrete structure may also be suitable for use as a wound packing material. A wound packing material is a material used to fill a cavity wound and is of particular use in conjunction with negative pressure wound therapy applications where a wound packing may be used to prevent a wound dressing from entering a wound cavity. For such applications, the knitted or woven structure may be produced with suitable dimensions, potentially in three dimensions.

The discrete structure may be a spacer fabric. Spacer fabrics are typically fabrics consisting of separate substrates which are spaced apart by spacer yarns. The spacer fabrics are typically knitted with knitted substrates spaced apart by spacer yarns formed from mono or multifilaments of yarn.

The discrete structure has a predetermined shape. The predetermined shape is preferably determined by the shape of the wound or body part to which the dressing is to be applied. The wound or body part may be measured prior to implementation of the method of the invention and the relevant dimensions inputted into the machine. The discrete structure may form part of a bespoke wound dressing.

The discrete structure may comprise a void suitable for incorporating an additional component of a wound dressing within said void. The size and shape of the void may be chosen to correspond to a specific component to be incorporated in the discrete structure. The void may be formed with an opening through which to insert the additional component or the void may be formed with the additional component in situ in which case the void may be sealed around the component thus fixing the component in place within the void.

The additional component may be any suitable component for incorporation within a wound dressing. For example the additional component may be a woven, knitted or nonwoven wound dressing component comprising medicaments, antimicrobial, antibacterial or antiseptic materials, or odour control materials. Alternatively or additionally the component may be a non-fabric component such as an electronic component, for example a pump for supplying negative pressure, a pressure monitor, a motion sensor or any suitable sensor for monitoring a wound site.

The machine of the first aspect may be controlled using a computer program product. Hence according to a fourth aspect of the invention is provided a computer program product comprising instructions to cause the machine of the third aspect to execute the steps of the method of the first aspect.

According to a fifth aspect of the invention is provided a non-transitory computer readable medium having stored thereon the computer program product of the fourth aspect.

According to an sixth aspect of the invention there is provided a system comprising at least one computing device, the computing device comprising:

at least one processor; and at least one memory storing instructions which, when executed by the at least one processor, cause the computer device to perform the method of the first aspect.

A schematic block diagram of an embodiment of a machine according to the third aspect of the invention is illustrated in FIG. 1. The machine may comprise a memory unit, a controller unit and a mechanical manipulator. The mechanical manipulator may be any suitable device such as a knitting machine or loom. Each of the elements may be remotely displaced from one another and connected via a suitable communication network. Suitable communication networks include local area networks (LAN) and wide area networks (WAN) and may be wired or wireless.

At least some of the example embodiments described herein may be constructed, partially or wholly, using dedicated special-purpose hardware. Terms such as 'component', or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components and units discussed herein, such functional elements may be combined into fewer elements or separated into additional elements.

According to an seventh aspect of the invention is provided the use of the component of the second aspect or produced by the method of the first aspect in or as a wound dressing, or the use of said component or wound dressing in a method of treating a wound.

Wound Dressing

Embodiments disclosed herein relate to apparatuses and methods of treating a wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body.

The disclosed technology may relate to preventing or minimizing damage to physiological tissue or living tissue, or to the treatment of damaged tissue e.g., a wound as described above.

As used herein the expression "wound" may include any injury to living tissue and may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound becomes a chronic wound when it does not follow the healing stages resulting in a lengthened recovery. It is believed that the transition from acute to chronic wound can be due to a patient being immuno-compromised.

Chronic wounds may include for example: Venous ulcers: Venous ulcers usually occur in the legs, account for the majority of chronic wounds, and mostly affect the elderly, Diabetic ulcers (typically foot or ankle ulcers, Peripheral Arterial Disease, Pressure ulcers, or Epidermolysis Bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

The wound may also include a deep tissue injury. The deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The wound may also include tissue at risk of becoming a wound as discussed above. For example, tissue at risk may include tissue over a bony protuberance (at risk of deep tissue injury/insult), pre-surgical tissue (e.g. knee) that may has the potential to be cut (for joint replacement/surgical alteration/reconstruction).

In some embodiments the disclosed technology relates to a method of treating a wound with the technology disclosed herein in conjunction with one or more of the following: advanced footwear, turning a patient, offloading examples such as diabetic foot ulcers, treatment of infection, systemix, antimicrobial, antibiotics, surgery, removal of tissue, affect blood flow, physiotherapy, exercise, bathing, nutrition, hydration, nerve stimulation, ultrasound, electrostimulation, oxygen therapy, microwave therapy, active agents ozone, antibiotics, antimicrobials, and the like.

The wound may be treated using topical negative pressure and/or traditional advanced wound care i.e., not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad e.g., a cushioning or compressive therapy (such as stocking or bandages).

In some embodiments treatment of such wounds can be performed using traditional wound care, wherein a dressing can be applied to the wound to facilitate and promote healing of the wound.

In some embodiments the disclosed technology relates to a method of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

The invention further provides a wound dressing which comprises or consists of the discrete structure produced according to the first aspect of the invention. Thus according to a second aspect of the invention there is provided a wound dressing comprising a discrete structure produced according to the first aspect of the invention.

Figure 2:
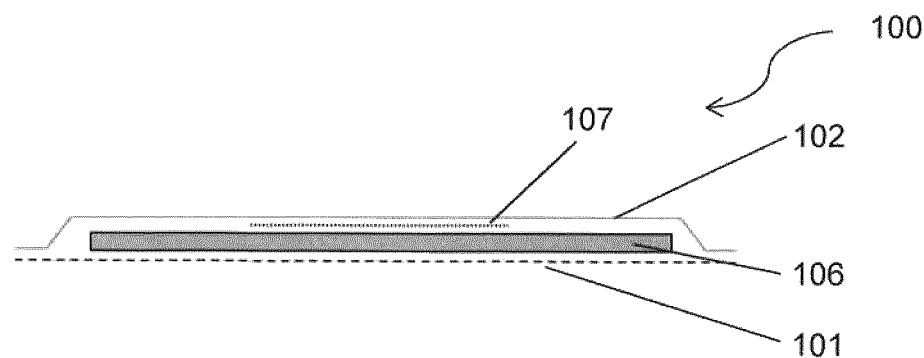
FIG. 2 illustrates a view through an embodiment of a wound dressing according to the invention.

Referring first to FIG. 2, there is shown a wound dressing generally designated 100 comprising a discrete structure produced according to the method of the first aspect of the invention or according to the second, third or fourth aspect of the invention.

Typically a wound dressing according to the invention may comprise a further absorbent layer or layers in addition to the discrete structure produced according to the first aspect of the invention. The additional absorbent layer may be a knitted or woven material, a foam, a superabsorbent or a combination thereof.

For the dressings according to the invention, the discrete structure may be contained between a wound contact layer and a top film.

The wound contact layer can comprise a perforated wound-side adhesive which can be a silicone adhesive, or a low-tack adhesive to minimise skin trauma on removal. The wound contact layer comprises a support material which can be a mesh, a net or a perforated film. It can also comprise a construction adhesive on the pad side, to ensure its intimate contact with the lowest part of the pad, and therefore efficient uptake of fluid from the wound without pooling.

The top film may be a liquid-impermeable, moisture-vapour permeable, breathable film, which allows moisture to evaporate from the dressing.

Figure 3:
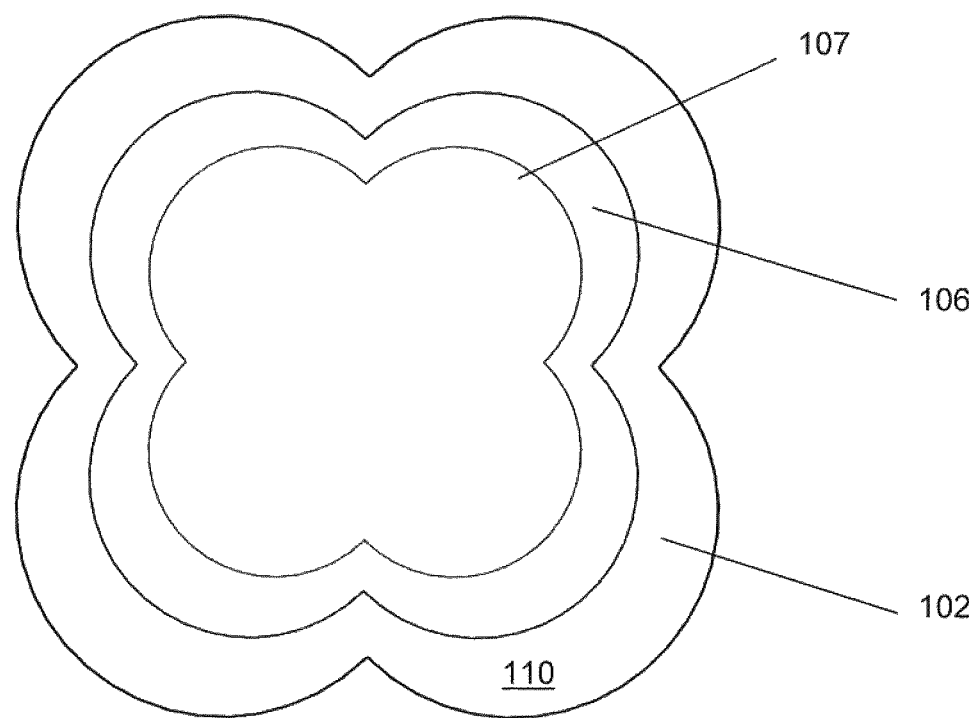
FIG. 3 illustrates a plan view of the dressing of FIG. 2.

FIGS. 2 and 3 respectively show a schematic cross-sectional view and a plan view of a wound dressing according to an embodiment of the present disclosure. The wound dressing 100 includes layers that are built up in a generally laminar fashion to form a dressing having a relatively planar form. The wound dressing 100 includes a border region 110 extending around the outer periphery of the dressing. The central region may be predetermined to suit a particular wound or particular wound type. There may be no border region required. Here the border region has the general function of providing an area for sealingly engaging with a patient's skin surrounding a wound site to form a sealed cavity over the wound site. The central region is the location of further functional elements of the wound dressing.

The dressing 100 includes a top film 102 and the discrete structure produced according to the first aspect of the invention 106, which in this case is a three-dimensional spacer fabric, providing protection from pressure.

Further components of the wound dressing 100 include:
A perforated wound contact layer 101.
A masking layer 107 to allow partial masking of the top surface of the discrete structure 106, where coloured exudate could remain.

Figure 4:
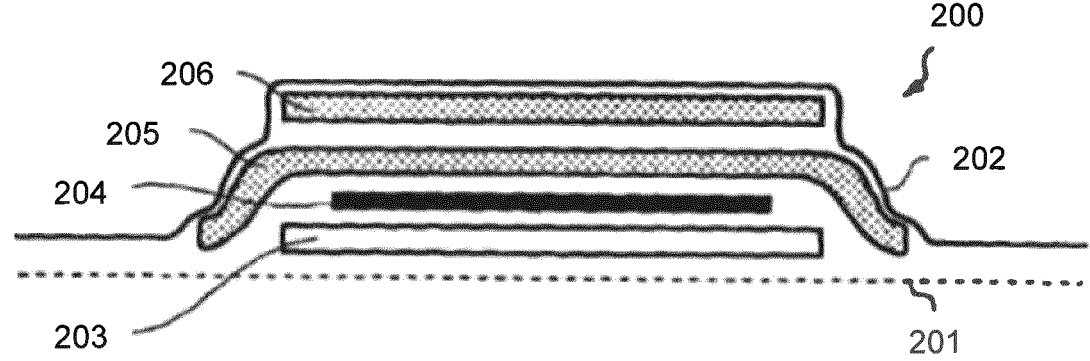
FIG. 4 illustrates a view through an embodiment of a wound dressing according to the invention
Figure 5A:
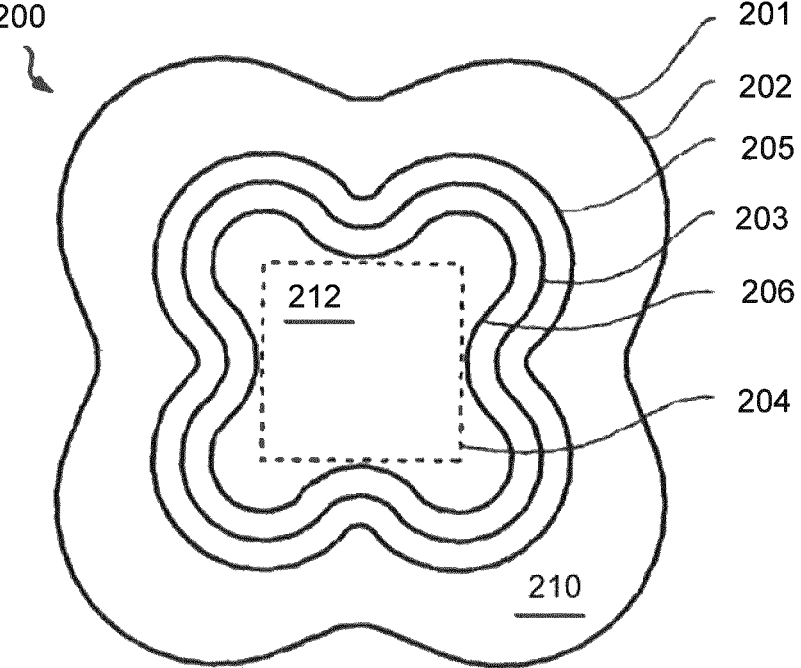
FIG. 5A illustrates a plan view of the dressing of FIG. 4
Figure 5B:
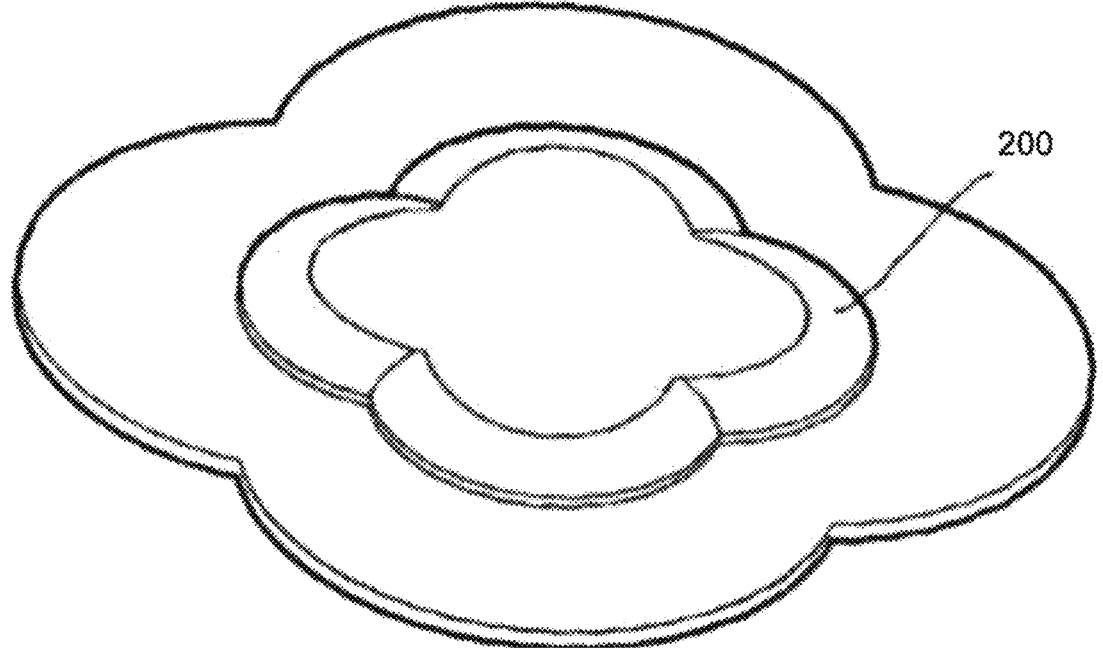
FIG. 5B illustrates a perspective view of the dressing of FIG. 4
Figure 6A:
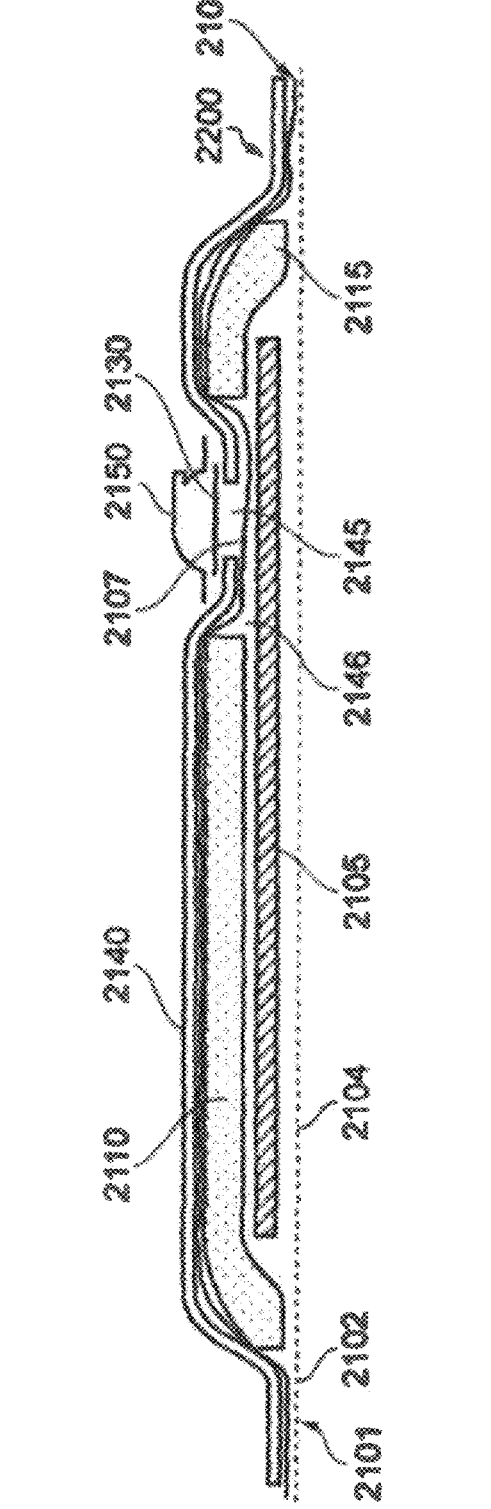
FIG. 6A illustrates a view through a further embodiment of a wound dressing according to the invention.
Figure 6B:
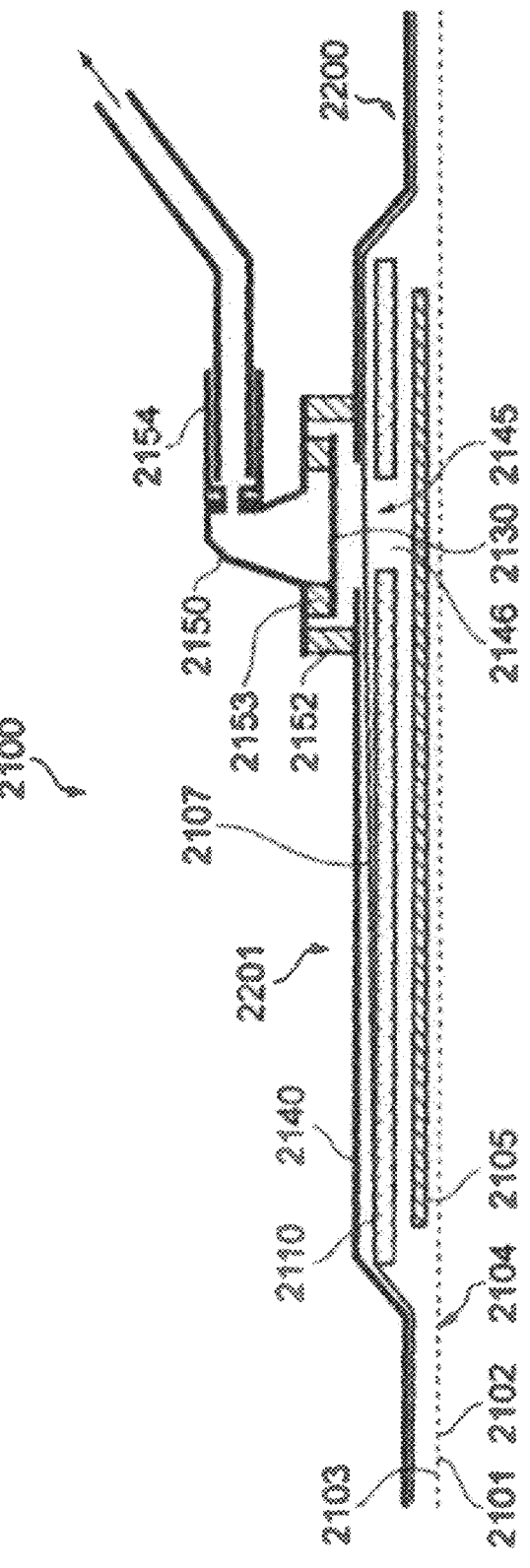
FIG. 6B illustrates a view through another embodiment of a wound dressing.
Figure 7:
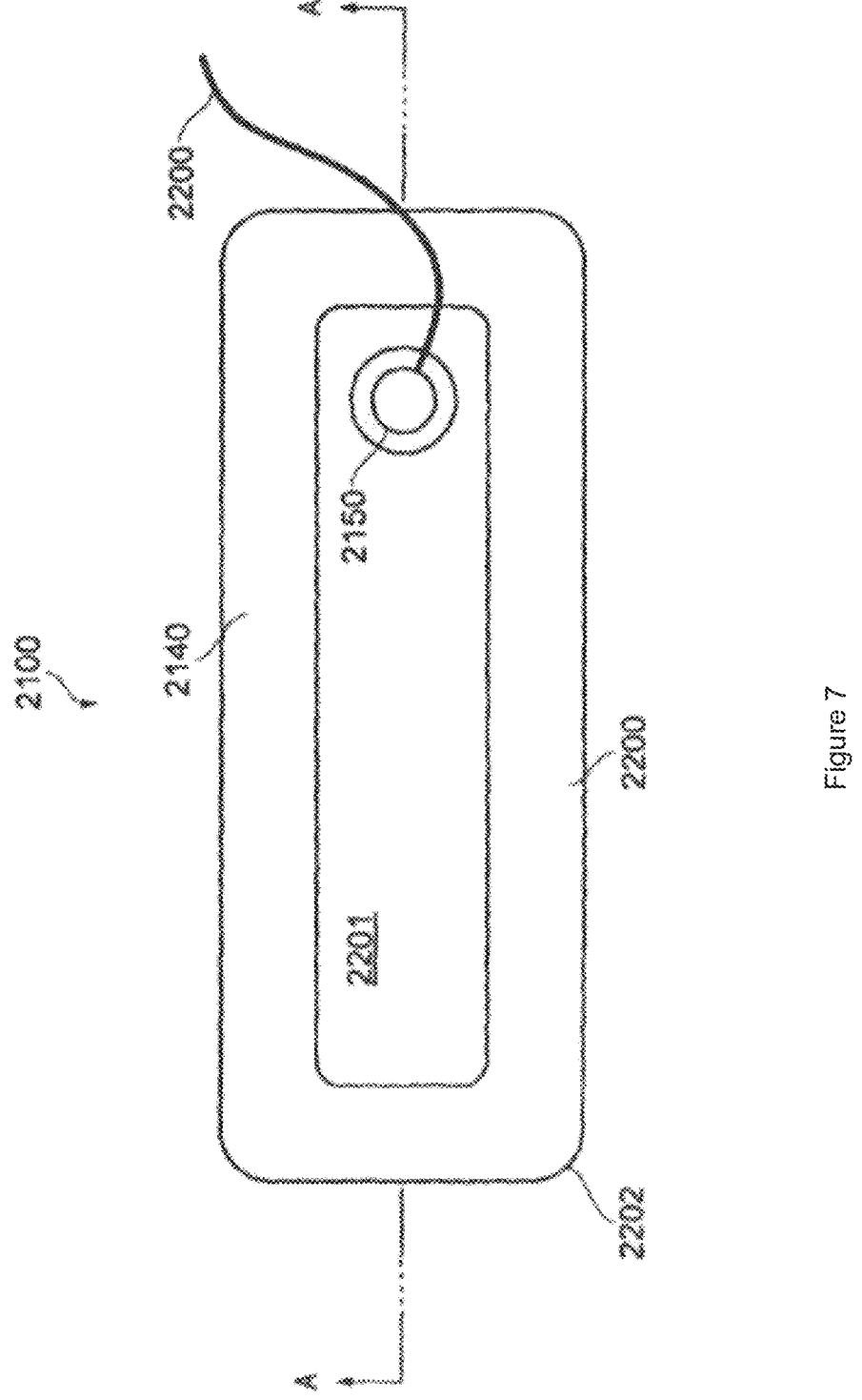
FIG. 7 illustrates a top view of an embodiment of a wound dressing.

FIGS. 4, 5A and 5B respectively show a schematic cross-sectional view, a plan view and a perspective view of a wound dressing according to a further embodiment of the present disclosure. The wound dressing 200 includes a number of layers that are built up in a generally laminar fashion to form a dressing having a relatively planar form. The wound dressing 200 includes a border region 210 extending around the outer periphery of the dressing. The central region may be predetermined to suit a particular wound or particular wound type. There may be no border region required. Here the border region has the general function of providing an area for sealingly engaging with a patient's skin surrounding a wound site to form a sealed cavity over the wound site. The central region is the location of further functional elements of the wound dressing.

The dressing 200 includes a top film 202 and the discrete structure produced according to the first aspect of the invention 206, which in this case is a three-dimensional spacer fabric, providing protection from pressure, while allowing partial masking of the top surface of the superabsorber, where coloured exudate would remain. Where appropriate, any of the additional components may also or alternatively be produced according to the method of the first aspect of the invention.

In this embodiment the discrete structure 206 is of smaller dimension (in plan view) than the layer 205, to allow for visibility of the edge of the absorbent layer, which can be used by clinicians to assess whether the dressing needs to be changed.

Further components of the wound dressing 200 include:
A perforated wound contact layer 201.
A layer of foam (203) of a suitable size to cover the recommended dimension of wounds corresponding to the particular dressing size chosen.
A layer of superabsorbent air-laid material (205) containing cellulose fibres and a superabsorbent polyacrylate particulates, of dimensions slightly larger than (203) to allow for an overlap of superabsorbent material acting as leak prevention.
A layer of activated charcoal cloth 204 of similar or slightly smaller dimensions than 103, to allow for odour control with limited aesthetic impact on the wound side.

The wound contact layer 201 may be a perforated polyurethane film that is coated with a skin-compatible adhesive, such as pressure sensitive acrylic adhesive or silicone adhesive (not shown). Alternatively the wound contact layer may be formed from any suitable polymer, e.g. silicone, ethyl-vinyl acetate, polyethylene, polypropylene, or polyester, or a combination thereof. The skin-compatible adhesive is coated on the lower side of the layer 201, i.e. the side that is to contact the patient.

The absorbent layer 203 of foam is located over the wound contact layer 201 and extends over the central region 212 of the wound contact layer.

The foam may be any suitable polymer foam. The foam is aptly a highly conformable hydrophilic foam, aptly an open celled foam, and more aptly the foam is a mixture of open and closed cells.

It is desirable that the foam layer absorbs the wound exudate rapidly. Such rapid absorption prevents undesirable pooling of exudate between the dressing and the wound.

The odour-removing layer of activated charcoal cloth 204 is provided over the layer of foam 203. In this embodiment the activated charcoal layer is about the same length and depth as the foam layer and therefore lies over the foam layer to cover about the same area. The layer may be of Zorflex® cloth available from Chemviron Carbon, for example. Alternative suitable materials are manufactured by MAST under the trade name C-TeX®.

The function of the odour-removing layer is to help prevent or reduce odour originating from the wound from transmitting out of the dressing.

The layer of absorbent material 205 is provided over the odour-removing layer 204. The absorbent layer 205 extends fully over the layer 204, as well as over the side portions of both the odour-removing layer 204 and the substrate having a protein immobilised thereon 203.

The layer 205 forms a reservoir for fluid, particularly liquid, removed from the wound site and draws those fluids towards a cover layer 202. The material of the absorbent layer also prevents liquid collected in the wound dressing from flowing freely once in the dressing structure. The second absorbent layer 205 also helps distribute fluid throughout the layer via a wicking action so that fluid is drawn from the wound site and stored throughout the absorbent layer, i.e. transferring and locking in the liquid. This prevents agglomeration in areas of the absorbent layer. The capacity of the absorbent material should be sufficient to manage the exudate flow rate of a wound for the predetermined life of the dressing, whether the wound is acute or chronic. Again, in combination with the substrate having a protein immobilised thereon, the layer 205 aptly should not cause the wound to become completely dry. This might occur if, for example, the superabsorbent material were to dry out the foam layer and then subsequently the wound area.

The discrete structure 206 is a spacer layer having a 3-dimensional structure. Additional spacer layers may also be incorporated and include open cell foam (e.g. Alleyvn™ foam by Smith & Nephew, Biatain foam by Coloplast or Advanced Medical Devices' ActivHeal foam), a knitted or woven spacer fabric (for example Baltex 7970 weft knitted polyester or Baltex XD spacer fabric or Surgical Mesh's Polyester felt or Polyester mesh) or a non-woven fabric (e.g. Fiberweb's S-tex or Securon). Alternatively the shielding layer may be a completely opaque polymer film having cut-out windows or perforations, for example (e.g. SNEF's H514 or H518 blue net).

Another function of the spacer layer 206 may be for pressure distribution and impact protection. For example, if the patient accidentally knocks the wound area, leans on the wound area or another cause applies a pressure to the dressing covering a wound. Aptly the shielding layer is provided closer to where the pressure is being applied than other layers of the dressing.

The spacer layer 206 may act as a pressure spreading component, receiving a pressure on one side thereof (possibly a point force) and spreading the pressure over a wider area, thus reducing the relative pressure received on the other side of the shielding layer. As such, the level of pressure felt by the patient at the wound site is reduced.

The top film 202 is a cover layer for covering the lower layers of the dressing, helping to encapsulate the layers between the wound contact layer and the top film. The top film 202 is in this case a layer of polyurethane, Elastollan (trade name) SP9109 manufactured by BASF. The top film may be coated with any suitable adhesive. Aptly the adhesive will be a pressure sensitive adhesive e.g. acrylic adhesive or silicone adhesive.

As such, the top film 202 helps to ensure that the dressing remains breathable, i.e. allows a proportion of fluid absorbed in the dressing to be evaporated via the outer surface of the dressing. In this way certain fluid content of the exudate can be transpired from the dressing, reducing the volume of remaining exudate and increasing the time before the dressing becomes full. Also, the top cover 202 helps to ensure that the border region 210 of the dressing remains breathable, i.e.

allows a patient's normal skin perspiration to be evaporated through the dressing, which helps in preventing or minimising skin maceration.

The outer layer of dressings of the present disclosure when present can be a continuous conformable film. The continuous moisture vapour transmitting conformable film outer layer of the wound dressing may be used to regulate the moisture loss from the wound area under the dressing and also to act as a barrier to bacteria so that bacteria on the outside surface of the dressing cannot penetrate to the wound area. Suitable continuous conformable films will have a moisture vapour transmission rate of at least 300, aptly from 300 to 5000 grams preferably 500 to 2000 grams/square meter/24 hrs at 37.5 C at 100% to 10% relative humidity difference. Such moisture vapour transmission rate of the continuous film allows the wound under the dressing to heal under moist conditions without causing the skin surrounding the wound to macerate.

In use, a wound dressing as described above would be applied to a wound site of a patient with the surface of the substrate according to the invention facing the wound site. Any wound exudate, blood or other wound fluid would travel into the dressing via the substrate according to the invention and sequential layers above the substrate according to the invention. Fluid would permeate through the foam layer, the activated charcoal layer, and then reach the absorber layer at which point preferably the liquid would not go any further and be retained by the absorber layer. On the other hand, gas and moisture vapour would be able to permeate further via the spacer layer and/or top film.

The wound facing surface of a wound dressing may be provided with a release coated protector (not shown in the figures), for example a silicon-coated paper. The protector covers the wound contacting side of the dressing prior to application to a patient, and can be peeled away at the time of use.

Various modifications to the detailed arrangements as described above are possible. For example, dressings according to the present disclosure do not require each of the specific layers as described above with respect to FIG. 2. Dressings may include only one layer, or any combination of the layers described above. Alternatively or additionally, the materials of the layers described above may be combined into a single layer or sheet of material to perform the functions of each layer by a single layer. The wound dressing may consist of the discrete structure or may consist of a top film and the discrete structure or of a top film, a wound contact layer and the discrete structure produced according to the first aspect of the invention.

As noted above, each of the layers described may be used to give one or more function to the wound dressing. As such, each of the layer materials may be used separately or in any combination such that each material provides the given function.

The wound contact layer described above is an optional layer. If used, a wound contact layer may be of any suitable material, such as polyethylene (or polyurethane as described above) or other suitable polymer, and may be perforated for example by a hot pin process, laser ablation process, ultrasound process or in some other way so as to be permeable to fluids.

Although the dressing described above has been described having a border region and a central region this need not be the case. The dressing may be provided without an adhesive layer for attachment to the skin of a patient. Rather, another means may be provided for locating the dressing at the correct position over a wound, such as adhesive tape or a tied bandage.

The relative widths of the various layers may be all the same or different to those as shown in the figures.

A wound dressing may be formed by bringing together the required layers. The method may include bringing layers together with adhesive over part or all of a layer. The method may be a lamination process.

Alternatively a wound dressing may be formed by bringing together layers as described with respect to FIG. 2 or FIG. 4, in a contiguous laminar stack, and adhering the top film to the wound contact layer in a border region.

The methods above may include bringing layers together with adhesive over part or all of a layer. The method may be a lamination process.

Alternatively a wound dressing may be formed by bringing together layers as described with respect to FIG. 2 or FIG. 4, in a contiguous laminar stack, and adhering the top film to the wound contact layer in a border region.

Any of the dressing embodiments disclosed herein can be used in with a source of negative pressure, such as a pump. Any of the dressing embodiments disclosed herein can also be used with a pump and a fluid or waste collection canister that can be put in fluid communication with the pump and the dressing so that the pump draws fluid or waste from the wound into the collection canister.

Additionally, in any embodiments, the pump can be a piezoelectric pump, a diaphragm pump, a voice coil actuated pump, a constant tension spring actuated pump, a manually actuated or operated pump, a battery powered pump, a DC or AC motor actuated pump, a combination of any of the foregoing, or any other suitable pump.

FIGS. 4A-B illustrate cross sections through a wound dressing 2100 according to an embodiment of the disclosure. A plan view from above the wound dressing 2100 is illustrated in FIG. 5 with the line A-A indicating the location of the cross section shown in FIGS. 4A and 3B. It will be understood that FIGS. 4A-B illustrate a generalized schematic view of an apparatus 2100. It will be understood that embodiments of the present disclosure are generally applicable to use in TNP therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

The wound dressing 2100, which can alternatively be any wound dressing embodiment disclosed herein including without limitation wound dressing 100 or 200 or have any combination of features of any number of wound dressing embodiments disclosed herein, can be located over a wound site to be treated. The dressing 2100 forms a sealed cavity over the wound site.

When a wound packing material is used, once the wound dressing 2100 is sealed over the wound site, TNP is transmitted from a pump through the wound dressing 2100, through the wound packing material, and to the wound site. This negative pressure draws wound exudate and other fluids or secretions away from the wound site. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer has a lower surface 2101 and an upper surface 2103. The perforations 2104 are through holes in the wound contact layer which enables fluid to flow through the layer.

A layer 2105 of porous material can be located above the wound contact layer. A discrete structure produced according to the first aspect of the invention in the form of a spacer fabric 2110 is provided above the porous material 2105. This spacer fabric 2110 allows transmission of fluid including liquid and gas away from a wound site into upper layers of the wound dressing. In particular, the spacer fabric 2110 ensures that an open air channel can be maintained to communicate negative pressure over the wound area even when the absorbent component has absorbed substantial amounts of exudates. The spacer fabric should remain open under the typical pressures that will be applied during negative pressure wound therapy as described above, so that the whole wound site sees an equalized negative pressure. The spacer fabric 2110 is has a three dimensional structure. Other additional spacer fabrics could of course be utilized. With reference to FIGS. 4A and 4B, a masking or obscuring layer 2107 can be positioned beneath the cover layer 2140. In some embodiments, the masking layer 2107 can have any of the same features, materials, or other details of any of the other embodiments of the masking layers disclosed herein, including but not limited to having any viewing windows or holes. Additionally, the masking layer 2107 can be positioned adjacent to the cover layer, or can be positioned adjacent to any other dressing layer desired. In some embodiments, the masking layer 2107 can be adhered to or integrally formed with the cover layer. In some embodiments the masking layer 2107 may optionally contain a hole (not shown) directly adjacent to the port 2150 to improve air flow through the layer.

A gas impermeable, but moisture vapour permeable, cover layer 2140 can extend across the width of the wound dressing, which can be any wound dressing embodiment disclosed herein including without limitation dressing embodiment 100 or have any combination of features of any number of wound dressing embodiments disclosed herein. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 2140 is sealed to the wound contact layer 2102 in a border region 2200 around the circumference of the dressing, ensuring that no air is drawn in through the border area, for example via adhesive or welding techniques. The cover layer 140 protects the wound from external bacterial contamination (bacterial barrier) and allows liquid from wound exudates to be transferred through the layer and evaporated from the film outer surface. The cover layer 2140 typically comprises two layers; a polyurethane film and an adhesive pattern spread onto the film. The polyurethane film is moisture vapour permeable and may be manufactured from a material that has an increased water transmission rate when wet.

The filter element 2130 may also include an odour absorbent material, for example activated charcoal, carbon fibre cloth or Vitec Carbotec-RT Q2003073 foam, or the like. For example, an odour absorbent material may form a layer of the filter element 2130 or may be sandwiched between microporous hydrophobic membranes within the filter element.

The filter element 2130 thus enables gas to be exhausted through the orifice 2145. Liquid, particulates and pathogens however are contained in the dressing.

The wound dressing 2100 and its methods of manufacture and use as described herein may also incorporate features, configurations and materials described in the following patents and patent applications that are all incorporated by reference in their entireties herein: U.S. Pat. Nos. 7,524,315, 7,708,724, and 7,909,805; U.S. Patent Application Publication Nos. 2005/0261642, 2007/0167926, 2009/0012483, 2009/0254054, 2010/0160879, 2010/0160880, 2010/0174251, 2010/0274207, 2010/0298793, 2011/0009838, 2011/0028918, 2011/0054421, and 2011/0054423; as well as U.S. application. Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation the wound dressing 2100 is sealed over a wound site forming a wound cavity. A pump unit applies a negative pressure at a connection portion 2154 of the port 2150 which is communicated through the orifice 2145 to the transmission layer 2105. Fluid is drawn towards the orifice through the wound dressing from a wound site below the wound contact layer 2102. The fluid moves towards the orifice through the transmission layer 2105. As the fluid is drawn through the transmission layer 2105 wound exudate is absorbed into the absorbent component 2110.

Turning to FIG. 5 which illustrates a wound dressing 2100 in accordance with an embodiment of the present disclosure one can see the upper surface of the cover layer 2140 which extends outwardly away from a centre of the dressing into a border region 2200 surrounding a central raised region 2201 overlying the transmission layer 2105 and the absorbent component 2110. As indicated in FIG. 5 the general shape of the wound dressing is rectangular with rounded corner regions 2202. It will be appreciated that wound dressings according to other embodiments of the present disclosure can be shaped differently such as square, circular or elliptical dressings, or the like.

With the embodiments of the present disclosure, a wound dressing is provided that helps improve patient concordance with instructions for use, helps improve patients' quality of life, and also helps a clinician observe and monitor a patient's wound.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Throughout the description and claims of this specification, the singular encompasses the plural unless the context otherwise requires. In particular, where the indefinite article is used, the specification is to be understood as contemplating plurality as well as singularity, unless the context requires otherwise.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," "essentially" and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Features, integers, characteristics, compounds, chemical moieties or groups described in conjunction with a particular aspect, embodiment or example of the present disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The readers attention is directed to all papers and documents which are filed concurrently with or previous to this specification in connection with this application and which are open to public inspection with this specification, and the contents of all such papers and documents are incorporated herein by reference.

The invention claimed is:

1. A method of manufacturing a planar wound dressing comprising:

mechanically manipulating a yarn with a machine to form a discrete structure having a predetermined shape and finished dimensions with finished edges;

incorporating the discrete structure as a layer in a planar wound dressing without altering the finished dimensions of the discrete structure; and providing at least one layer above or below the discrete structure layer in the planar wound dressing.

2. A wound dressing formed according to the method of claim 1.

3. The wound dressing of claim 2 wherein the discrete structure is a spacer fabric layer.

4. The wound dressing of claim 3 wherein the wound dressing is a negative pressure wound dressing.

5. The wound dressing according to claim 4 wherein at least a portion of the discrete structure retains its integrity on application of negative pressure in the presence of wound exudate.

6. The wound dressing of claim 2 wherein the discrete structure comprises an absorbent yarn.

7. The wound dressing of claim 6 wherein the absorbent yarn is distributed through the discrete structure in a predetermined pattern.

8. The wound dressing of claim 6 wherein the absorbent yarn is laid into the discrete structure.

9. The method of claim 1 wherein the yarn includes an absorbent yarn.

10. The method of claim 9 wherein the step of mechanically manipulating the yarn comprises distributing the absorbent yarn through the discrete structure in a predetermined pattern.

11. The method of claim 1 wherein the yarn includes a first yarn and an absorbent yarn.

12. The method of claim 11 wherein the step of mechanically manipulating the yarn comprises knitting at least the first yarn and laying-in the absorbent yarn into the knitted first yarn.

13. The method of claim 1 wherein the discrete structure is formed by knitting or weaving the yarn.

14. The method of claim 1 wherein the predetermined shape is determined by the shape of a wound or body part to which the dressing is to be applied.

15. A wound dressing formed according to the method of claim 1 wherein the discrete structure comprises a void suitable for incorporating an additional component of the wound dressing within said void.

16. The method of claim 1 wherein the discrete structure is incorporated in the planar wound dressing as a spacer fabric layer.

17. The method of claim 1 wherein the discrete structure comprises a void suitable for incorporating an additional component of the planar wound dressing within said void.

18. The method of claim 1 wherein the at least one layer comprises a cover layer above the discrete structure layer.

19. The method of claim 1 wherein the at least one layer comprises a wound contact layer below the discrete structure layer.

20. The method of claim 1 wherein the at least one layer comprises a cover layer above the discrete structure and a wound contact layer below the discrete structure layer.

* * * * *